(12) United States Patent
Fontanarosa et al.

(10) Patent No.: US 10,870,019 B2
(45) Date of Patent: Dec. 22, 2020

(54) RADIATION THERAPY SYSTEM USING PLURAL TREATMENT PLANS

(71) Applicant: KONINKLIJKE PHILIPS N.V., Eindhoven (NL)

(72) Inventors: Davide Fontanarosa, Neerpelt (BE); Alfonso Agatino Isola, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 354 days.

(21) Appl. No.: 15/742,575

(22) PCT Filed: Jul. 6, 2016

(86) PCT No.: PCT/EP2016/065888
§ 371 (c)(1),
(2) Date: Jan. 8, 2018

(87) PCT Pub. No.: WO2017/005758
PCT Pub. Date: Jan. 12, 2017

(65) Prior Publication Data
US 2018/0200536 A1    Jul. 19, 2018

(30) Foreign Application Priority Data
Jul. 9, 2015    (EP) .................... 15176043

(51) Int. Cl.
*A61N 5/10*    (2006.01)
(52) U.S. Cl.
CPC .......... *A61N 5/1067* (2013.01); *A61N 5/1037* (2013.01); *A61N 5/1049* (2013.01);
(Continued)

(58) Field of Classification Search
CPC ...................... A61N 5/1037; A61N 5/103–107
See application file for complete search history.

(56) References Cited

U.S. PATENT DOCUMENTS 5,427,097 A * 6/1995 Depp .................. A61N 5/1049
600/427
8,135,111 B2    3/2012 Jaffray et al.
(Continued)

FOREIGN PATENT DOCUMENTS

EP    1977788 A2    10/2008
EP    2540346 A1    1/2013
(Continued)

OTHER PUBLICATIONS

D.W. Litzenberg et al., "Prostate Intrafraction Translation Margins for Real-Time Monitoring and Correction Strategies", Prostrate Cancer, vol. 2012, Article ID 130579.

*Primary Examiner* — Thaddeus B Cox

(57) ABSTRACT

The invention relates to a system for delivering a radiation treatment to a structure (21) within a body. In the system, a plurality of treatments plans is provided, each treatment plan being associated to one of a plurality of predefined possible position (33a; 33b) of the structure (21), which area regularly distributed on at least one predefined surface (32a; 32b). A control unit is configured to determine the position of the structure during the treatment and to select a treatment plan which is associated with a predefined possible position having a smallest distance to the determined position, for controlling the radiation source in response to the detection of the position. Moreover, the invention relates to a computer program for controlling the system and to a planning unit for generating the treatment plans.

20 Claims, 2 Drawing Sheets

(52) U.S. Cl.
CPC .................. *A61N 2005/105* (2013.01); *A61N 2005/1055* (2013.01); *A61N 2005/1058* (2013.01); *A61N 2005/1061* (2013.01)

(56) References Cited

U.S. PATENT DOCUMENTS

| | | |
|---|---|---|
| 2009/0041188 A1 | 2/2009 | Keall et al. |
| 2011/0009761 A1* | 1/2011 | Ruan .................... A61B 5/1135 600/529 |
| 2013/0021602 A1 | 1/2013 | Dribinski et al. |
| 2013/0216026 A1 | 8/2013 | Nord |
| 2014/0270077 A1* | 9/2014 | Etmektzoglou ........ A61N 5/107 378/65 |
| 2016/0016007 A1 | 1/2016 | Bharat et al. |
| 2016/0310761 A1* | 10/2016 | Li ........................ A61N 5/1038 |

FOREIGN PATENT DOCUMENTS

| | | |
|---|---|---|
| WO | 2007014106 A2 | 2/2007 |
| WO | 2015/038832 | 3/2015 |
| WO | 2015/103184 | 7/2015 |

\* cited by examiner

RADIATION THERAPY SYSTEM USING PLURAL TREATMENT PLANS

CROSS-REFERENCE TO PRIOR APPLICATIONS

This application is the U.S. National Phase application under 35 U.S.C. § 371 of International Application Serial No. PCT/EP2016/065888, filed on Jul. 6, 2016, which claims the benefit of European Patent Application No. 15176043.6, filed on Jul. 9, 2015. This application is hereby incorporated by reference herein.

FIELD OF THE INVENTION

The invention generally relates to radiation therapy delivered to patients particularly in order to treat cancer. More specifically, the invention relates to a system and to a method for delivering a radiation treatment to a structure within a human or animal body.

BACKGROUND OF THE INVENTION

In external beam radiation therapy, ionizing radiation is applied to target structures, such as tumors, within patients' bodies in order to control growth of or kill cancer cells. The radiation treatment is usually delivered in plural sessions, which are also referred to as treatment fractions in the art. In more advanced types of radiation therapy, such as so called intensity-modulated radiation therapy, precise doses of radiation (usually x-ray radiation) are applied to tumors or specific areas within a tumor in each fraction. These treatments are planned in a so-called inverse planning procedure. In this procedure, the structures or regions to be treated within a patient's body are identified and target radiation doses are specified for each structure. Then, an optimization process is carried out to find the treatment plan which allows for delivering the target radiation doses to the identified structures. This treatment plan particularly specifies the number and duration of the treatment fractions and the configuration of the radiation source (including, for example, the radiation dose to be emitted, the shape of the radiation beam and the target locations within the patient's body) in each fraction. Typically, this configuration is specified in the form of so-called control points, where each control point is associated with values for the relevant parameters of the radiation source.

One factor limiting the quality of radiation therapy, particularly in case of intensity-modulated radiation therapy, is motion of the structure to be treated within the patient's body. So, intra-fraction displacements (i.e. displacements during one treatment fraction) of more than 1 cm have been found for the prostate, which is often treated by radiation therapy to cure prostate cancer. As a result of such a motion, the actual position of the structure to be treated does not correspond to the position for which the treatment plan and the included control points have been generated. Thus, the treatment plan becomes inaccurate and radiation is delivered to the incorrect regions with within the patient's body. Therefore, it would be desirable to compensate for displacements of the structure to be treated during the treatment.

In this respect, the publication D. W. Litzenberg et al., "Prostate Intrafraction Translation Margins for Real-Time Monitoring and Correction Strategies", Prostate Cancer, Volume 2012, Article ID 130579 (accessible online via http://dx.doi.org/10.1155/2012/130579), discloses a radiation therapy system comprising a tracking unit for tracking the prostate during radiation therapy treatment using transponders implanted into the prostate. When a motion or a displacement of the prostate is detected, the systems allows for moving the prostate to compensate for the displacement by moving the patient table supporting the patient during the treatment.

Although this system allows for re-positioning the prostate at the location assumed in the treatment plan, it does not make it possible to compensate for all relevant changes resulting from prostate motion. So, a displacement of the prostate does also change the tissue configuration. More specifically, the radiation beam may have to traverse more or less tissue or other types of tissue within the body to reach the prostate after the displacement. Since the tissue configuration is one factor taken into account when generating the control points of the treatment plan, the aforementioned changes of the tissue configuration would also have to be compensated for in order to fulfill the treatment plan. Otherwise, there is particularly a risk that healthy tissue receives a higher radiation dose. However, it is not possible to compensate for such changes of the tissue configuration by moving the patient table.

US 2013/021602 relates to a system for providing intensity modulated radiation therapy to a moving target. For a movement of the target along a predicted breathing path, the system generates a treatment plan which comprises a plurality of sub-plans each of which is optimized for a different phase of the target movement and takes into account the next phase of the movement. During the radiation treatment, the movement of the target is tracked and, based on the position of the target, the system selects a corresponding sub-plan for carrying out the treatment.

SUMMARY OF THE INVENTION

Therefore, it is an object of the invention to allow for an improved adaption of a radiation therapy treatment to motions of the structure to be treated, particularly to intra-fraction motion occurring during the radiation treatment.

In a first aspect of the invention, a system for delivering a radiation treatment to a structure within a body is suggested. The system comprises a radiation source for providing the radiation applied to the structure, a control unit for controlling the radiation source in accordance with a treatment plan, and a localization unit for determining the position of the structure within the body during the radiation treatment. Further, a plurality of treatments plans is provided, each treatment plan being associated to one of a plurality of predefined possible positions of the structure and the predefined possible positions being regularly distributed on at least one predefined surface. The control unit is configured to determine the position of the structure during the treatment and to select a treatment plan, which is associated with a predefined possible position having a smallest distance to the determined position, for controlling the radiation source in response to the detection of the position.

Since plural treatment plans are provided for several possible positions of the structure to be treated and since the radiation therapy system is capable of selecting the treatment plan pertaining to the possible position having the smallest distance to the determined position of the structure, the radiation treatment can be adapted to different positions of the structure. And, in case of a motion of the structure during the radiation treatment, the radiation therapy system can change from one treatment plan to another treatment plan which is better adapted to the new position of the structure. Further, it is particularly also possible to compensate for changes of the tissue configuration due to a motion of the structure as each treatment plan can be adapted to the tissue configuration at the associated position of the structure. Thus, it is possible in response to a detected displacement of the structure to change to a new treatment plan, which is adapted to the changed tissue configuration at the new position of the structure.

The possible shifted positions are regularly distributed on the at least one predefined surface. In this regard, it has turned out that such a regular distribution of the shifted positions on one or more surfaces allows for an especially suitable spatial distribution of the shifted positions in view of possible displacements of the structure to be treated during the treatment.

In one embodiment, a first treatment plan is associated with a reference position of the structure and further treatment plans are associated with predefined possible shifted positions of the structure, the reference position corresponding to a position determined using measurement data. In particular, the reference position may be determined using three-dimensional images of the structure as in conventional radiation therapy systems. The images may be acquired using a computed tomography (CT) or magnetic resonance imaging (MRI) device, for example. In this case, the measurement data correspond to the acquired image data.

The position of the structure to be treated is preferably parameterized by means of a position of a reference point of the structure. In one embodiment, the reference point of the structure may correspond to an estimated center of mass of the structure. In particular, the estimated center of mass may be used as the reference point of the structure if the position of the structure is determined on the basis of images. In this case, the contour of the structure may be determined on the basis of the images and the center of mass may be calculated on the basis of the contour.

In a further embodiment, the control unit is configured to use the first treatment plan associated with the reference position when the radiation treatment (i.e. one treatment fraction in case plural treatment fractions are provided) is initiated. This first treatment plan corresponds to the treatment plan that would also be used in a conventional radiation therapy system using only a single treatment plan for controlling the radiation treatment. Often, this treatment plan is the most appropriate treatment plan at the beginning of the radiation treatment and is therefore initially selected in this embodiment.

A related embodiment provides that the control unit is configured to select a further treatment plan only in case it is determined that a distance between the determined position and the reference position exceeds a predetermined threshold. This embodiment does particularly simplify the detection of a situation in which the control unit changes from the first treatment plan to a further treatment plan.

In a further embodiment, the control unit is configured to determine the position of the structure to be treated before starting the radiation treatment (i.e. one treatment fraction in case plural treatment fractions are provided) and to select the treatment plan associated with the predetermined position having the smallest distance to the determined position before the treatment. Then, the control unit may initiate the radiation treatment using the selected treatment plan.

In one embodiment, at each predefined possible shifted position of the structure, a reference point of the structure is located on the at least one surface.

The predefined surface(s) may surround the reference point of the structure at the reference position. The surface(s) may particularly be configured as closed surfaces enclosing the reference position. In a related embodiment, the predefined surfaces correspond to concentric spheres or ellipsoids centered at the reference point of the structure at the reference position. With respect to these embodiments, it has been found that the location of possible shifted positions on suitable surfaces, such as, for example, spheres or ellipsoids, allows for an improved spatial distribution of the shifted position compared with other spatial patterns.

The motion of the structure may or may not involve a privileged direction, along which the structure moves with a higher probability compared to the probability for movements along other directions. If there is no privileged direction, the surface comprising the shifted positions may particularly be configured as spheres. In case there is a privileged direction, they may particularly be configured as ellipsoids. In this regard, one embodiment provides that directions of major axes of the ellipsoids correspond to a direction in which the structure moves with a probability that is higher than a probability for movements of the structure in other directions. Moreover, further embodiments provide that the surface corresponds to a closed surface in which certain regions are excluded. These excluded regions may correspond to areas to which the structure to be treated moves with a probability below a threshold.

In one embodiment, the control unit is configured to determine positions of the structure on the basis of the images generated by the localization unit. In particular, the control unit comprises a pattern recognition unit configured to localize the structure within the images generated by the localization unit to determine the position of the structure or the control unit may be capable of recognizing the structure by comparing the images with a reference image in which the structure is delineated.

In a further related embodiment, the localization unit comprises an imaging unit for generating three-dimensional images of a region of the body including the structure to be treated. In a related embodiment, the imaging unit comprises one unit of the group including a computed tomography unit, a magnetic resonance imaging unit and an ultrasound unit.

The structure to be treated by means of the radiation therapy system may include a prostate. However, the system may also be used for delivering a radiation treatment to another structure within a body.

In a further aspect, the invention suggests a computer program executable in a processor of a radiation therapy system. The computer program comprises instructions, which when executed by the processor cause the processor to carry out a method for controlling the radiation therapy system when the computer program is executed in the processor, the radiation therapy system comprising a radiation source for providing the radiation applied to the structure, a control unit for controlling the radiation source in accordance with a treatment plan, and a localization unit for determining the position of the structure within the body during the radiation treatment. The method comprises:

providing to the control unit a plurality of treatments plans, each treatment plan being associated to one of a plurality predefined possible positions of the structure and the predefined possible positions being regularly distributed on at least one predefined surface, the control unit determining the position of the structure during the treatment, and the control unit selecting a treatment plan, which is associated with a predefined possible position having a smallest distance to the determined position of the structure, for controlling the radiation source in response to the detection of the position.

In a further aspect of the invention, a planning unit for generating treatment plans for controlling a radiation treatment to a structure within a body in a radiation therapy system as described above is suggested. The planning unit is configured to generate a first treatment plan based on a reference image of the structure and to generate further treatment plans for controlling the radiation treatment of the structure on the basis of deformed versions of the reference image, wherein the structure is located at a reference position in the reference image and wherein the structure is located at one of a plurality of predefined possible shifted positions in each of the deformed versions of the reference image, the predefined possible shifted positions corresponding to possible positions of the structure during the treatment and being regularly distributed on at least one predefined surface.

In one embodiment, the planning unit is included in the radiation therapy system described above. Further, the planning unit is configured to provide the generated treatment plans to the control unit of the radiation therapy system, in one embodiment.

It shall be understood that the radiation therapy system of claim 1, the computer program of claim 14 and the planning unit of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
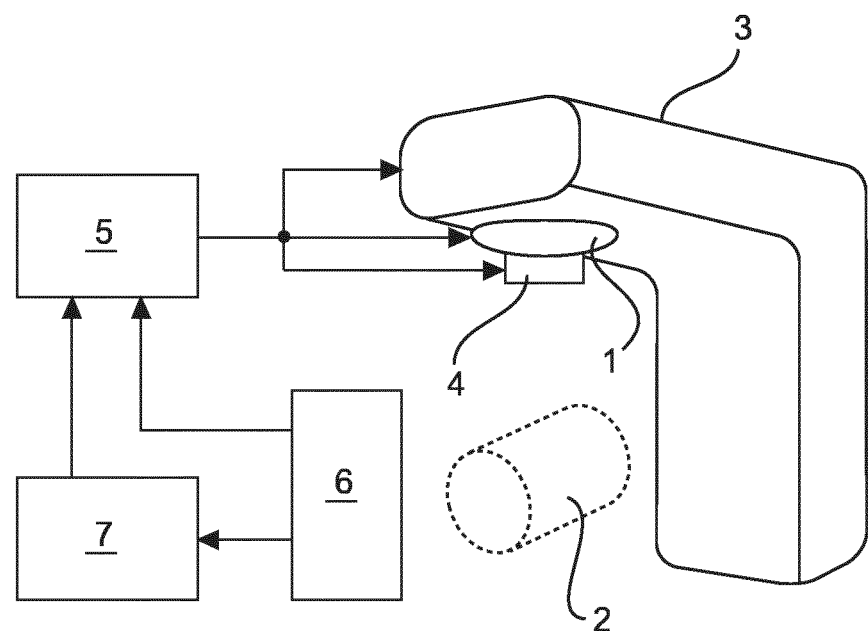
FIG. 1 schematically and exemplarily shows components of an embodiment radiation therapy system for delivering a radiation treatment to a structure within a body, FIG. 2 schematically and exemplarily illustrates a deformation region of an image of a prostate including an image volume which is deformed in order to determine treatment plans for shifted positions of the prostate, and FIG. 3 schematically and exemplarily illustrates a trajectory of a of reference point of a prostate during a motion of the prostate and a predefined shifted positions of the reference point to which treatment plans are associated.

FIG. 1 schematically and exemplarily illustrates an embodiment of a radiation therapy system for delivering radiation treatments to structures within a human or animal body. In particular, the system may be used to treat tumors within certain structures of the body. One example of such a structure is the prostate as it is known that radiation therapy is especially suitable for treating prostate cancer.

In the illustrated embodiment, the radiation therapy system comprises a radiation source 1, which can be operated to emit ionizing radiation to be delivered to a tumor or another diseased structure within a human or animal body positioned in a treatment zone 2 of the system. For supporting the body within the treatment zone, the system may comprise a patient table. The relative position and orientation of the radiation source 1 with respect to the body can be varied over a certain range of positions and orientations. For this purpose, the radiation source 1 may be mounted on rotatable gantry 3 so that the radiation source 1 can be rotated around the treatment zone or body within a certain angular range, which may be 360° or less. Thus, radiation can be delivered to the body from different angular positions. Further, the body can be moved relative to the gantry 3 so that radiation can be delivered to different parts of the body regarding its longitudinal extension. In order to achieve that, the gantry 3 and/or the patient table may be movable back and forth in a direction parallel to the rotation axis of the gantry 3.

The radiation source 1 may include an x-ray tube or a linear particle accelerator for producing one ionizing radiation beam (in further embodiment, the radiation system may produce several radiation beams in a similar way). The radiation source 1 is controllable in order to vary the intensity and/or energy of the radiation beam. Further, the radiation source 1 may be provided with a collimator 4 for shaping the radiation beam. The collimator 4 may likewise be controllable in order to vary the radiation beam shape.

For controlling the radiation source 1, the collimator 4 (if controllable) and the patient table (if moveable), the system includes a controller 5. During a radiation therapy treatment, the controller 5 controls the relative position and orientation of the radiation source 1 and the body by positioning the gantry 3 and/or the patient table. Further, the controller 5 controls the intensity and energy of the radiation beam and (if possible) the radiation beam shape. Preferably, the controller 5 is implemented in a processor including a microprocessor for executing a control program comprising the control routines carried out by the controller 5.

In addition, the radiation therapy system comprises a localization unit 6 for localizing the structure to be treated within the patient body during a radiation treatment. In one embodiment, the localization unit 6 includes and imaging device, which produces images of the body in accordance with a suitable imaging modality. In this respect, the localization unit 6 may include an ultrasound device, a computed tomography (CT) device, a magnetic resonance imaging (MRI) device or a fluoroscopy imaging unit, for example. Such devices are known to a person skilled in the art as such and, thus, they are not described in greater detail herein. By means of such a device, the localization unit 6 produces a three-dimensional image of the body region including the structure to be treated. In these images, the structure may be identified by means of a suitable pattern recognition algorithm executed in the localization unit 6. In further embodiments, the localization unit 6 may also be configured in a different way. For instance, the localization unit 6 may be configured to localize the structure to be treated using transponders implanted into the structure as described in the publication by D. W. Litzenberg et al. mentioned above.

The radiation treatment of the structure with the body may be performed during a plurality of fractions, where the fractions may be delivered to the structure on consecutive days or in another cycle. In order to deliver one fraction to the structure within the body, the body is positioned in the treatment zone 2 of the radiation therapy system in such a way that a reference mark on the body is located at a defined position relative to the radiation source 1. For this purpose, the body can be positioned on the patient table and aligned with the help of an alignment unit of the radiation therapy system. The alignment unit may include a laser positioning device which is known to the skilled person as such and, thus, will not be described in greater detail herein. Upon having positioned the body in treatment zone, the controller 5 controls the delivery of radiation to the structure to be treated. In so doing, the controller 5 aligns the radiation source 1 and controls the further parameters of the radiation source 1 in accordance with a treatment plan stored in the controller 5 for the treatment of the specific body structure.

The treatment plan defines the irradiation parameters for the radiation treatment of the structure. These parameters include the alignment of the radiation source 1, which is defined in view of defined position of the reference mark on the body during the treatment. Moreover, the parameters may include further information, such as the energy and intensity of the radiation beam and (if variable) the shape of the radiation beam, for each fraction of the radiation treatment. During the radiation treatment one or more parameters usually change. So, the relative alignment of the radiation source 1 and the body may be changed, for example, by rotating the gantry around the body, and in this process also the beam shape may be adapted to each position of the radiation source 1 or the gantry 3. The changes of the irradiation parameters specified in the treatment plan are often also referred to as control points. Thus, the treatment plan comprises a series of control points which are successively delivered during the radiation treatment, where the delivery of a control point corresponds to the delivery of radiation in accordance with the irradiation parameters to which the treatment plan changes at the respective control point. For each control point, the treatment plan may also specify a time interval during which the respective control point is delivered. Upon expiration of this time interval, the controller 5 delivers the succeeding control point of the treatment plan.

Within the scope of the present invention, a plurality of treatment plans are provided for the treatment of a specific body structure and stored in the controller 5, and the controller 5 can change from one treatment plan to another treatment plan in a way described in more detail herein below. These treatment plans may be generated in a semi-automated process using a planning unit 7 which is preferably implemented in a computer device and which may be coupled to the radiation therapy system in such a way that the treatment plans can be provided to the controller 5 of the radiation therapy system to be stored therein. Preferably, the treatment plans are particularly generated on the basis of a three-dimensional image—which is also referred to as reference image herein—of the body region including the structure to be treated. Therefore, the planning unit 7 may particularly include means for displaying the image to a physician or another operator and for receiving inputs by the operator with respect to the image. Further, the planning system may dispose of routines for planning a radiation treatment, which are particularly capable of generating a treatment plan for delivering a specified radiation dose (which may be defined by an operator) to a specific structure located at a fixed position within a body.

One of the provided treatment plans—which is also referred to as first treatment plan herein—may be generated in a conventional way known to a person skilled in the art on the basis of the reference image. For this purpose, the structure to be treated may be identified in the planning unit 7. In particular, the contour of this structure may be marked in this image. This may be done on the basis of a corresponding input by a physician that may mark the contour in the image using a suitable input means and/or by an automated pattern recognition routine executed in the planning unit 7. Further, the overall radiation dose to be delivered to the structure is specified. For this purpose, the radiation dose may be set by physician, for example. Then, the planning system 7 generates the first treatment plan on the basis of the location of the structure to be treated within the body and on the basis of the specified overall radiation dose. In this process, the planning system 7 particularly defines the fractions of the radiation treatment and the control points for each of the fractions. In one embodiment, this is done in an automated process on the basis of automated routines implemented in the planning unit 7. Such routines are known to a person skilled in the art as such and, thus, are not described in greater detail herein. One example of such routines are included in the auto-planning option of the commercially available radiation therapy planning system Pinnacle offered by Philips Healthcare.

In addition to the first treatment plan, further treatment plans are generated by means of the planning unit 7. These further treatment plans are provided in view of possible motions of the structure to be treated within the body. In particular, the further treatment plans are provided in view of possible intra-fraction motion of the structure, i.e. motion occurring during delivery of one fraction of the radiation treatment. In this respect, intra-faction motions with displacements of more than 1 cm have been observed for the prostate, for example. Without compensating for such motions, there would be a high risk that the radiation dose delivered to the tumor to be treated would be too low, while the radiation dose delivered to healthy tissue surrounding the tumor would be too high. Moreover, it has been found that such prostate motions tend to increase over time. Therefore, additional fixed margins in the treatment plan are not suitable in order to compensate for such motions, because a fixed margin would over-compensate at the beginning of the fraction and would under-compensate at the end of the fraction. Before this background, the provision of treatment plans for a plurality of positions of the structure allows for a suitable compensation of a displacement of the structure within the body, when the control unit changes from one treatment plan to another treatment plan upon a determined displacement of the structure during a treatment fraction.

Preferably, the further treatment plans are generated for a plurality of possible shifted positions of the structure within the body, i.e. positions differing from the position of the structure shown in the reference image. In this regard, the position of the structure may particularly be defined by a position of a reference point of the structure, which preferably corresponds to an estimated center of mass of the structure. This estimated center of mass may be calculated on the basis of the contour of the structure identified in the reference image and on the basis of the assumption that the structure has a homogeneous mass density. However, it is likewise possible to define the position of the structure on the basis of another reference point which does not correspond to the structure's center of mass.

In one embodiment, the considered shifted positions are characterized in that at each shifted position, the reference point of the structure is located on one or more surface(s) surrounding the position of the reference point as shown in the reference image—this position is also referred to as reference position herein. Then, one three-dimensional image is produced for each of the shifted positions of the structure. Here, an image for a shifted position may be generated on the basis of the reference image by deforming the reference image or a region thereof in such a way that the structure is located at the shifted position. Subsequently, one treatment plan is generated for each of the shifted positions on the basis of the three-dimensional produced for the respective shifted positions. The generation of the treatment plans may be done in the same way as the generation of the first treatment plan. In particular, the treatment plans may be generated by an automated routine of the planning system 7 on the basis of the generated images and the information about the overall radiation dose (which is the same as the overall radiation dose on the basis of which the first treatment plan is generated).

The surface(s), on which the shifted positions of the reference point are located, may be closed surfaces enclosing the reference position of the reference point. Further, the surface(s) are preferably determined on the basis of privileged directions of motion of the structure, i.e. directions along which the structures moves with a higher probability than the probability for movements along other directions. Such privileged directions may be empirically determined for each relevant type of structure based on clinical experience. If such a privileged direction exists, each of the one or more surface(s) may correspond to an ellipsoid with a major axis that is larger than a minor axis, where the major axis may extend along the privileged direction of the movements of the structure within the body. Optionally, it is also possible to discard certain regions of the surface, i.e. to refrain from locating shifted positions in such regions, if the probability that the reference point of the structure moves towards such regions is zero or very low. In case no privileged direction exists for the movement of the structure, each of the one or more surface(s) may correspond to a sphere. In this respect, more recent studies have suggested that the motion of the prostate follows a three-dimensional random walk model and does not have a privileged direction. In that far, one or more sphere(s) may be used in case the structure is a prostate, and the center(s) of the sphere(s) may correspond to the reference position of the reference point of the structure.

When plural surfaces are used, there may be a predetermined distance between the surfaces and between the innermost surface and the reference position of the reference point of the structure. In one embodiment, the distance may be between 0.2 and 0.6 cm, particularly the distance may be 0.4 cm. On the basis of this distance, the number of surfaces may be selected in view of the expected maximum displacement of the structure. Thus, in case the structure is a prostate moving up to more than 1 cm, two spheres with radii of 0.4 cm and 0.8 cm may be defined in one embodiment.

Within each of the surfaces, the predetermined shifted positions of the reference point of the structure to be treated are preferably regularly distributed. This particularly means that each shifted position on one of the surfaces has certain predetermined distances to the adjacent shifted positions on the surface, where the predetermined distance is substantially the same for all shifted positions on the same surface. In case certain regions of the surface do not include shifted positions due to a low probability that the reference point of the structure moves to this region of the surface, the shifted positions are preferably distributed regularly on the remaining regions of the surface. In order to generate shifted positions which are regularly distributed on the surface, the controller 9 may use a so-called recursive polyhedral subdivision mechanism, which is e.g. described in the publication C. Smith, "On Vertex-Vertex Systems and Their Use in Geometric and Biological Modelling", Dissertation at the University of Calgary, Canada, 2006. In accordance with such a mechanism, each surface may be approximated by a polygon mesh in several steps, where the polygons of the mesh are subdivided into smaller polygons in each step in order to better approximate the surface. Here, the corners of the polygons form vertices arranged on the surface, and the shifted positions of the reference point of the structure to be treated may correspond to theses vertices in one embodiment. However, it is likewise possible that the shifted positions are defined on the surfaces in another way.

In further embodiments, the shifted positions of the reference point of the structure are not determined on the basis of one or more predetermined surfaces but on the basis of other spatial patterns. For instance, the shifted positions of the reference point may be defined using a rectangular three-dimensional point grid, where one shifted position may be located at each grid point. However, compared with definition of the shifted positions using a rectangular grid, the definition of the shifted position using predetermined surfaces, particularly spheres or ellipsoids, allows for an improved spatial distribution of the shifted positions in view of possible motions of the structure to be treated.

Figure 2:
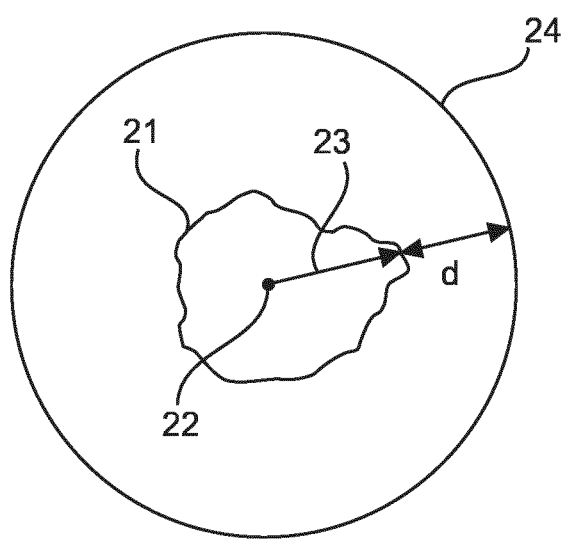

In order to generate the images for the shifted positions of the structure from the reference image, it is in principle possible that the planning unit 7 calculates a deformation of the complete reference image for each shifted position. However, in order to reduce the computational complexity, a deformation may only be calculated for a certain part of the reference image—which is also referred to as deformation region herein—for each of the shifted positions. In one embodiment, the deformation region may correspond to the image volume included in a sphere centered at the reference point of the structure. The radius of the sphere is preferably selected based on the dimensions of the structure to be treated and on the basis of the maximum of the distances between the reference position and the shifted positions of the structure. In particular, the radius may be set larger than the maximum radius of the structure (i.e. the maximum distance between the reference point of the structure and its contour) plus the maximum of the distances between the reference position and the shifted positions of the structure. This ensures that the sphere includes the complete structure at all shifted positions. When the structure is a prostate and when the shifted positions are determined as explained above (i.e. the maximum distance between the reference position and the shifted positions is 0.8 cm), the sphere may have a radius corresponding to the maximum radius of the prostate determined in the reference image plus 2 cm, for example. This is further illustrated in FIG. 2, which schematically and exemplarily shows the contour of a prostate 21 in an image. Further, FIG. 2 shows the estimated center of mass 22 of the prostate 21 and its maximum radius is marked by means of an arrow 23. In addition, FIG. 2 illustrates the deformation region bounded by the sphere 24. The radius of the sphere 24 is larger than the maximum radius of the prostate by an amount d, which may be 2 cm, for example.

As said above, deformations of the reference image may only be calculated within the deformation region. The image volume outside the deformation region is not deformed in this case. In the deformation process relating to one shifted position, the planning unit 7 calculates a deformation or motion field which may specify a distance and a direction of displacement for each image element of the reference image (i.e. for each so-called voxel). In accordance with this deformation field, the voxel including the reference point of the structure to be treated is moved (as one constraint of the deformation process) to the shifted position. In one embodiment, the other voxels of the structure to be treated may be moved using the same motion vector as the voxel comprising the reference point of the structure. This means that all voxels of the structure are moved in the same direction and over the same distance. In further embodiments, also a rotation and/or a deformation of the structure is/are additionally calculated. For this calculation, the mechanical properties of the body regions surrounding the structure and empirical observations of motions of structure of the same type may be taken into consideration. In addition to the movement of the structure, the voxels of the surrounding body regions within the deformation region are moved in accordance with the movement of the structure. For these voxels of the surrounding body regions, it is likewise possible to use the same motion vector used for moving the voxel including the reference point of the structure. However, in order to a achieve a more accurate deformation, it is preferred to take deformations of the surrounding body regions into account which may be calculated on the basis of the mechanical properties of these body regions and on the basis of empirical observations of the motion of structure of the relevant type.

Upon having determined the deformation field describing the changes of the deformation region due to the motion of the structure, the planning unit 7 preferably adapts the motion vectors in a boundary area of the deformation region in order to create smooth transitions between voxels outside and inside the deformation region in the deformed image. For this purpose, the planning unit 7 may apply a suitable interpolation technique. In particular, a kernel interpolation may applied, which may use a trilinear or thin-plate spline kernel.

In such a way, the planning unit generates a deformed image for each of the previously defined shifted positions of the reference point of the structure to be treated. As already explained above, a treatment plan is then generated for each shifted position of the reference point on the basis of the deformed image associated with the respective shifted position. In so doing, the planning unit 7 generates a collection of treatment plans for the shifted positions of the structure to be treated. This collection of treatment plans, which also includes the treatment plan generated on the basis of the reference image, is forwarded to the controller 5 of the radiation therapy system in order to be used for controlling the system during the radiation treatment of the structure.

For carrying out the treatment, the relative alignment of the body or the structure to be treated is preferably set in accordance with the first treatment plan and the reference image. Then the radiation treatment fraction is initiated on the basis of the first treatment plan in one embodiment.

During the radiation treatment, the controller 5 monitors the position of the structure to be treated in order to detect any displacements of the structure relative to the reference position. For this purpose, the reference position determined by the planning system 7 during the process for planning the treatment is indicated to the controller 5. Further, the localization unit 6 is operated during the treatment in order to acquire data indicative of the position of the structure at successive points in time. In case the localization unit 6 comprises an imaging device, these data correspond to images of a body region comprising the structure to be treated. In each image, the controller 5 determines the contour of the structure to be treated by means of a pattern recognition routine. This routine may particularly identify structures and its contours using a corresponding classifier which may be established in a suitable training process. In a further embodiment, the controller 5 uses the reference image of the structure for determining shifted positions of the structure during the radiation treatment. In particular, the controller 5 may deform the reference image such that the contour of the structure to be treated is brought in conformity with the corresponding contour in an image acquired during the radiation treatment. As a result of this process, which involves less complex calculations than an automatic recognition of the structure to be treated in the images acquired during the radiation treatment, the controller 5 is capable of identifying the position of the structure and its reference point in each image acquired during the radiation treatment. Upon having identified the contour of the object to be treated, the controller 5 estimates the reference point of the structure in the same way as the planning unit 7 estimated the reference point in the reference image. In such a way, the controller 5 determines the positions of the reference point of the structure at successive points in time.

On the basis of the determined position, the controller 5 may generally select the treatment plan which is associated with the position of the reference point having the shortest distance to the determined positions. For this purpose, the distance between the determined positions and positions to which a treatment plan is associated may be calculated using a suitable distance measure. In one embodiment, an Euclidean distance measure is used. However, it is likewise possible to use another distance measure known to a person skilled in the art.

In order to carry out the selection of the treatment plan, the controller 5 may compare each determined position of the reference point of the structure with its previously determined position (or, at the beginning of the treatment, with the reference position) in one embodiment. In case it detects a displacement of the reference point of the structure, the controller 5 compares the determined position with the positions to which treatment plans are associated and selects from these positions the one having the shortest distance to the determined positions.

In a further embodiment, the aforementioned comparison between the position determined in the current step and the previously determined position is dispensed with. In this embodiment, the controller 5 directly compares the determined position of the reference point with the positions to which treatment plans are associated in order to select the one of these positions that has the shortest distance to the determined position of the reference point. If the treatment plan associated with the selected position in accordance with one of the aforementioned selection procedures corresponds to the treatment plan that is currently used, the controller 5 maintains this treatment plan and further controls the radiation treatment on the basis of this plan. If the treatment plan associated with the selected position does not correspond to the treatment plan currently in use, the controller 5 changes the treatment plan and further controls the radiation treatment using the treatment plan associated with the selected position. This procedure may be repeated during the complete treatment fraction, so that the treatment plan is changed each time the structure changes its position in such a way that the reference point is brought close to a different position to which a treatment plan is associated.

In principle, the controller 5 can execute the aforementioned procedure during the complete treatment fraction starting at the beginning of the fraction. In a further embodiment, which is particularly applicable in case the shifted positions of the structure are located on a sphere or ellipse, the controller 5 only changes from the first treatment plan used at the beginning of the treatment to a further treatment plan if it determines that the displacement of the reference point of the structure with respect to its reference position is larger than a threshold value. In one embodiment, the threshold value may correspond to the half radius or the half minimum radius (e.g. in case the surface corresponds to an ellipsoid) of the innermost surface on which the shifted positions are located.

Thus, after the initiation of the treatment fraction, the controller 5 monitors the position of the reference point of the structure to be treated as explained above and checks for each determined position, whether the distance between this position and reference position is larger than the threshold. If this is not the case, the controller 5 maintains the first treatment plan loaded at the beginning of the treatment fraction. Only if the controller 5 determines that the distance between the position of the reference point determined in one step and the reference position is larger than the threshold, it searches for the predefined shifted position which has the smallest distance to the determined position. Then, the controller 5 selects the treatment plan pertaining to the ascertained shifted position and uses this treatment plan to further control the radiation treatment of the structure.

Upon such a first change of the treatment plan, the controller 5 may then proceed as explained above. This means that the controller 5 may keep on monitoring the position of the reference point of the structure may select the treatment plan associated with the predefined shifted position having the shortest distance to the determined position for each determined position (this may or may not involve a change from a previously used treatment plan to a new treatment plan).

Figure 3:
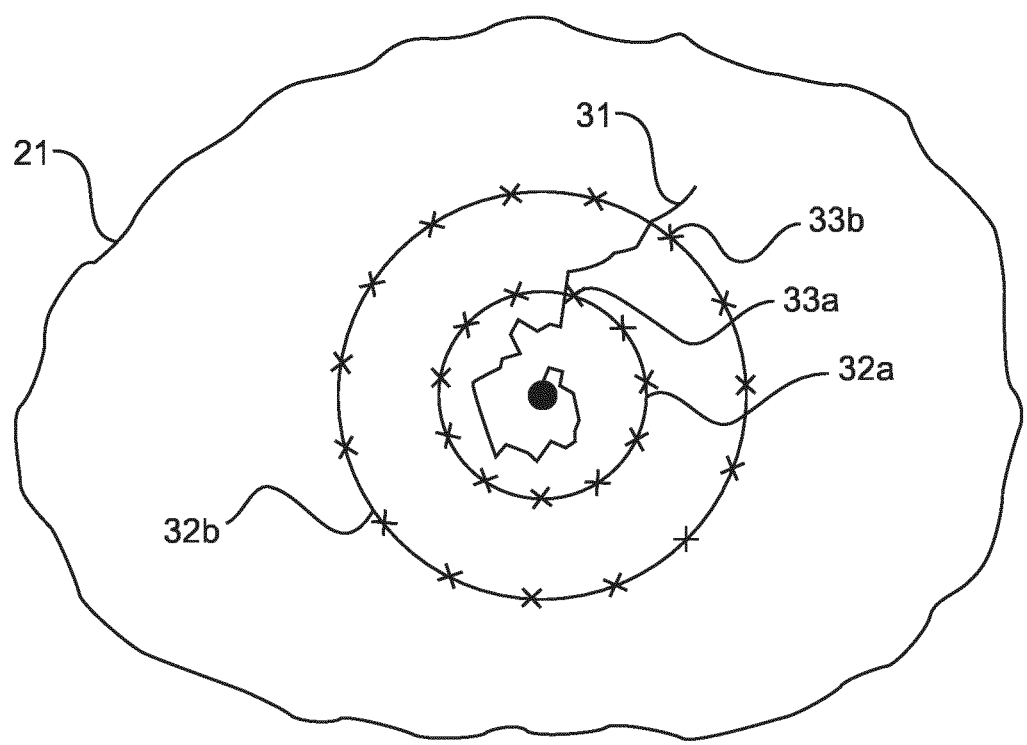

FIG. 3 further illustrates the aforementioned procedure for a motion of a prostate 21. Under the assumption that the prostate motion follows a random walk model, FIG. 3 exemplary shows an exemplary trajectory 31 of the center of mass 22 of the prostate during a radiation treatment. Further, FIG. 1 illustrates two surfaces 32a, 32b including predefined shifted positions of the reference point to which treatment plans are associated. The surfaces 32a, 32b are configured as spheres and the shifted positions are marked by means of crosses in FIG. 3. As can be seen in FIG. 3, the trajectory 31 is located within the volume bounded by the innermost surface 32a at the beginning of the treatment and, thus, the distance between the positions of the reference point and the center of mass (used as there reference point of the prostate 21) is smaller than the threshold value corresponding to the radius of the innermost surface 32. In this situation, the controller 5 uses the first treatment plan for controlling the radiation treatment. Then, at a certain point in time, the trajectory 31 crosses the innermost surface 32a. This may be detected by the controller 31 when it determines that the difference between the position of the reference point and the reference position exceeds the threshold value. In response to this determination, the controller 5 changes from the first treatment plan to the treatment plan for the shifted position 33a, which is the shifted position having the smallest distance to the position of the reference point in this situation. Thereupon, the trajectory 31 runs towards the outer surface 32b and crosses this surface 32b at a certain point in time. During this course of the trajectory 31, the controller 5 changes from the treatment plan associated with the shifted position 33a to the treatment plan associated with the shifted position 33b, when it determines that the determined position of the reference point is closer to the shifted position 33b than to the shifted position 33a. A change of the treatment plan is preferably effected by the controller 5, when one control point of the treatment plan has been completely delivered. Then the controller 5 delivers the next control point in accordance with the new treatment plan selected on the basis of the comparison between the determined position of the reference point of the structure to be treated and the predetermined shifted positions of the reference point. In this respect, all treatment plans preferably comprise the same timing with respect to the control points so that the consecutive control points are valid for the same time intervals in all treatment plans. This ensures that the controller 5 can completely deliver a new control point after the change to a new treatment plan upon the complete delivery of a preceding control point of the former treatment plan.

In related embodiment, the determination of the actual position of the reference point of the structure (as described above) and the process for selecting a treatment plan is synchronized with the timely sequence of the control points in the treatment plans. In this embodiment, the controller 5 may determine the position of the reference point of the structure and select the treatment plan pertaining to the closest predetermined position once in each of the time intervals associated with the control points of the treatment plans. Moreover, the process of determining the positions of the reference point and selecting the treatment plan pertaining to the closest position may be timed by the controller 5 such that it is completed shortly before the next control point is to be delivered.

However, also another timing of the aforementioned process is possible. So, the controller 5 may execute the process in fixedly predefined time intervals, for example. Moreover, changes of the treatment plan may not be effected upon having completely delivered one control point. In alternative embodiments, the controller 5 may rather change to a new treatment plan during a time interval for delivering a certain control point in response to a determination that the reference point of the structure is closest to the predetermined position associated with this treatment plan.

Furthermore, the first treatment plan is used at the beginning of a treatment fraction in the aforementioned embodiments. In alternative embodiments, the controller 5 determines the position of the reference point of the structure before the actual radiation treatment fraction is initiated (i.e. before radiation is applied to the structure). Then, the controller 5 determines the predetermined positions having the smallest distance to the detected position of the reference point. Thereupon, the controller 5 may begin the treatment fraction using the selected treatment plan. During the treatment fraction, the controller 5 can then change to one or more further treatment plan(s) in a manner explained above.

Of course, it is also possible that a new planning procedure is carried out in the planning unit 7 before a treatment fraction is delivered. This planning procedure may be executed based on a determined current position of the structure to be treated and preferably takes into account the radiation doses delivered to the structure during the preceding treatment fractions. In this planning procedure, the planning unit 7 does preferably generated a new collection of treatments plans and the further treatment fractions can be delivered on the basis of this new collection of treatment plans in a way described above.

Thus, in conclusion, a radiation therapy system is provided which uses a collection of treatment plans in order to compensate for motion of the structure to be treated during the treatment. In this respect, the invention is not limited to the embodiments of the radiation therapy system described above. So, it is particularly possible to radiation source 1 which are configured and/or mounted in another way. Further, it is particularly possible to user another localization unit 6 as long as this localization unit allows for determining the position of a reference point of the structure to be treated during the radiation treatment.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for delivering a radiation treatment to a structure within a body, the system comprising:
a radiation source for providing radiation in accordance with the radiation treatment to the structure;
a controller adapted to control the radiation source in accordance with a treatment plan; and
a localization unit adapted to determine a position of a reference point of the structure within the body during the radiation treatment, the controller being configured to determine the position of the reference point of the structure during the treatment and to select a treatment plan, which is associated with a predefined possible position of the reference point having a smallest distance to the determined position, for controlling the radiation source in response to a detection of the position, wherein a plurality of treatment plans is provided, each of the plurality of treatment plans being associated with one of a plurality of predefined possible positions of the reference point of the structure and the predefined possible positions being regularly distributed on at least one predefined surface.

2. The system as defined in claim 1, wherein a first treatment plan is associated with a reference position of the reference point of the structure and further treatment plans are associated with predefined possible shifted positions of the reference point of the structure, the reference position corresponding to a position determined using measurement data.

3. The system as defined in claim 2, wherein the controller is configured to use the first treatment plan associated with the reference position when the radiation treatment is initiated.

4. The system as defined in claim 3, wherein the controller is configured to select a further treatment plan in case it is determined that a distance between the determined position and the reference position exceeds a predetermined threshold.

5. The system as defined in claim 3, wherein the at least one predefined surface surrounds the reference point of the structure at the reference position.

6. The system as defined in claim 2, wherein predefined surfaces correspond to concentric spheres or ellipsoids centered at the reference point of the structure at the reference position.

7. The system as defined in claim 1, wherein the reference point of the structure corresponds to an estimated center of mass of the structure.

8. The system as defined in claim 7, wherein directions of major axes of ellipsoids correspond to a direction in which the structure moves with a probability that is higher than a probability for movements of the structure in other directions.

9. The system as defined in claim 1, wherein the localization unit comprises an imaging unit for generating three-dimensional images of a region of the body including the structure.

10. The system as defined in claim 9, wherein the controller is configured to determine positions of the reference point of the structure on a basis of the images generated by the localization unit.

11. The system as defined in claim 9, wherein the imaging unit comprises one unit of a group including a computed tomography unit, a magnetic resonance imaging unit and an ultrasound unit.

12. The system as defined in claim 1, wherein the structure within the body comprises a prostate.

13. A planning unit for generating treatment plans for controlling a radiation treatment to a structure within a body in a radiation therapy system according to claim 1, the planning unit being configured to generate a first treatment plan based on a reference image of the structure and to generate further treatment plans on a basis of deformed versions of the reference image, wherein the reference point of the structure is located at a reference position in the reference image and wherein the reference point of the structure is located at one of a plurality of predefined possible shifted positions in each of the deformed versions of the reference image, the predefined possible shifted positions corresponding to possible positions of the reference point of the structure during the treatment and being regularly distributed on at least one predefined surface.

14. A radiation therapy system comprising:
a radiation source for providing radiation to a structure;
a controller comprising a processor, and adapted to control the radiation source in accordance with a treatment plan;
a localization unit for determining a position of the structure within a body during a radiation treatment;
a tangible, non-transitory computer readable medium that stores instructions, which when executed by the processor, cause the processor to perform a method, comprising:
providing to the controller a plurality of treatment plans, each of the plurality of treatment plans being associated with one of a plurality of predefined possible positions of a reference point of the structure and the predefined possible positions being regularly distributed on at least one predefined surface;
determining the position of the reference point of the structure during the treatment; and
selecting a treatment plan, which is associated with a predefined possible position having a smallest distance to the determined position of the reference point of the structure, for controlling the radiation source in response to a detection of the position.

15. A tangible, non-transitory computer readable medium that stores instructions, which when executed by a processor, cause the processor to:
provide to a controller a plurality of treatment plans, each of the plurality of treatment plans being associated with one of a plurality of predefined possible positions of a reference point of a structure and the predefined possible positions being regularly distributed on at least one predefined surface;

determine a position of the reference point of the structure during a radiation treatment; and select a treatment plan, which is associated with a predefined possible position having a smallest distance to the determined position of the reference point of the structure, for controlling a radiation source in response to a detection of the position.

16. The tangible, non-transitory computer readable medium as defined in claim 15, wherein a first treatment plan is associated with a reference position of the reference point of the structure and further treatment plans are associated with predefined possible shifted positions of the reference point of the structure, the reference position corresponding to a position determined using measurement data.

17. The tangible, non-transitory computer readable medium defined in claim 16, wherein the instructions, when executed by the processor cause the processor to use the first treatment plan associated with the reference position when the radiation treatment is initiated.

18. The tangible, non-transitory computer readable medium as defined in claim 17, wherein the instructions, when executed by the processor cause the processor to select a further treatment plan in case it is determined that a distance between the determined position and the reference position exceeds a predetermined threshold.

19. The tangible, non-transitory computer readable medium as defined in claim 17, wherein the at least one predefined surface surrounds the reference point of the structure at the reference position.

20. The tangible, non-transitory computer readable medium as defined in claim 15, wherein the reference point of the structure corresponds to an estimated center of mass of the structure.

* * * * *